(12) United States Patent
Staehlin et al.

(10) Patent No.: US 6,488,686 B2
(45) Date of Patent: Dec. 3, 2002

(54) BONE CUTTING AND BREAKING APPARATUS, AND MINIATURIZED CUTTING HEAD

(75) Inventors: John H. Staehlin, New Windsor, MD (US); David S. Hungerford, Cockeysville, MD (US)

(73) Assignee: Volunteers for Medical Engineering, Baltimore, MD (US)

( * ) Notice: Subject to any disclaimer, the term of this patent is extended or adjusted under 35 U.S.C. 154(b) by 7 days.

(21) Appl. No.: 09/784,177

(22) Filed: Feb. 16, 2001

(65) Prior Publication Data

US 2001/0034525 A1 Oct. 25, 2001

Related U.S. Application Data

(62) Division of application No. 09/377,403, filed on Aug. 20, 1999, now Pat. No. 6,309,394.
(60) Provisional application No. 60/097,332, filed on Aug. 20, 1998.

(51) Int. Cl.[7] .............................................. A61B 17/32
(52) U.S. Cl. ........................................ 606/80; 606/180
(58) Field of Search ........................... 606/80, 170, 167, 606/180; 433/110, 111, 120, 132; 415/503

(56) References Cited

U.S. PATENT DOCUMENTS

| | | | |
|---|---|---|---|
| 3,678,943 A | | 7/1972 | Noel et al. |
| 3,962,789 A | * | 6/1976 | Flatland ........................... 32/27 |
| 4,281,989 A | * | 8/1981 | Glover et al. ................ 433/130 |
| 4,860,735 A | | 8/1989 | Davey et al. |
| 4,966,552 A | * | 10/1990 | Gonser .......................... 433/132 |
| 5,041,119 A | | 8/1991 | Frigg et al. |
| 5,211,645 A | | 5/1993 | Baumgart et al. |
| 5,340,311 A | * | 8/1994 | Sakurai ......................... 433/126 |
| 5,478,093 A | | 12/1995 | Eibl et al. |
| 5,645,545 A | | 7/1997 | Bryant |

\* cited by examiner

*Primary Examiner*—Eduardo C. Robert
(74) *Attorney, Agent, or Firm*—Finnegan, Henderson, Farabow, Garrett & Dunner L.L.P.

(57) ABSTRACT

The present invention includes an apparatus and method for cutting a bone including a cutting assembly having a cutting blade, a cutting guide for guiding the shape of the cut in the bone, and a power source for powering the cutting blade. The cutting blade is moveable radially to vary the depth of the cut in the bone, and the cutting blade is capable of cutting around the circumference of the bone as well as in a longitudinal direction along the bone. A powered bone breaking device for completing the breaking of the weakened bone is also disclosed. A miniaturized version of the bone cutting apparatus can be used to cut out sections of a femur head from inside a femur body.

9 Claims, 22 Drawing Sheets

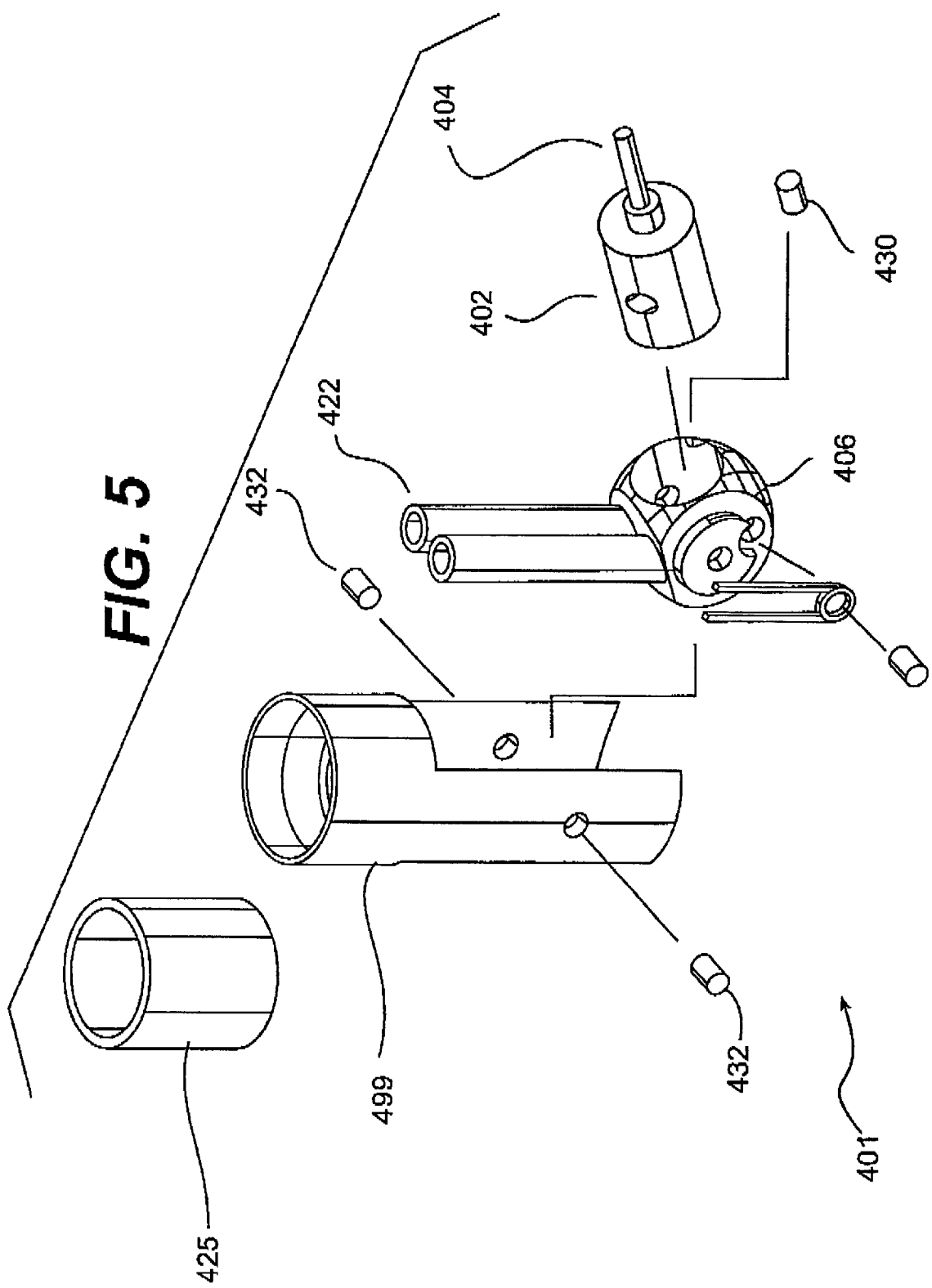

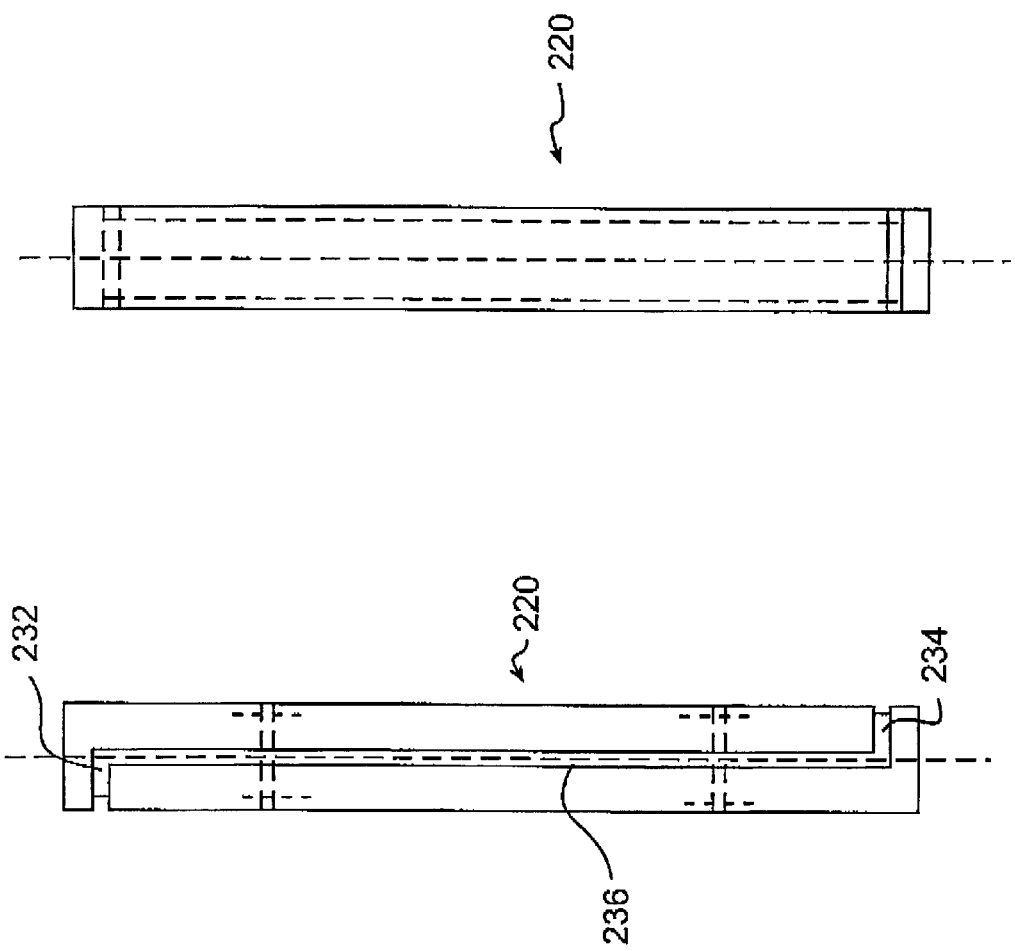

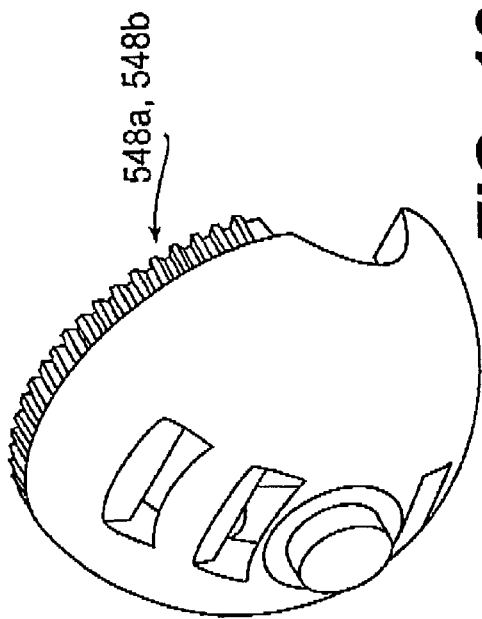
FIG. 13C
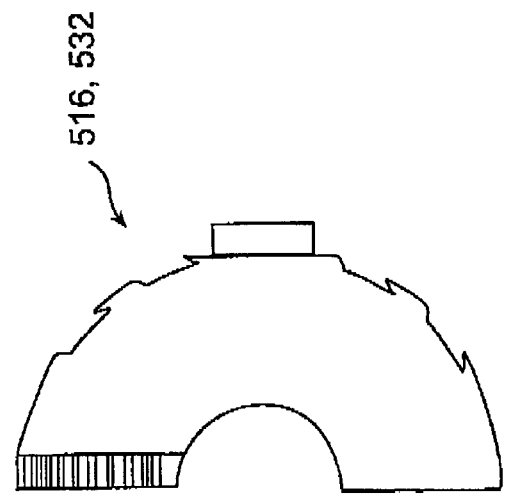
FIG. 13D
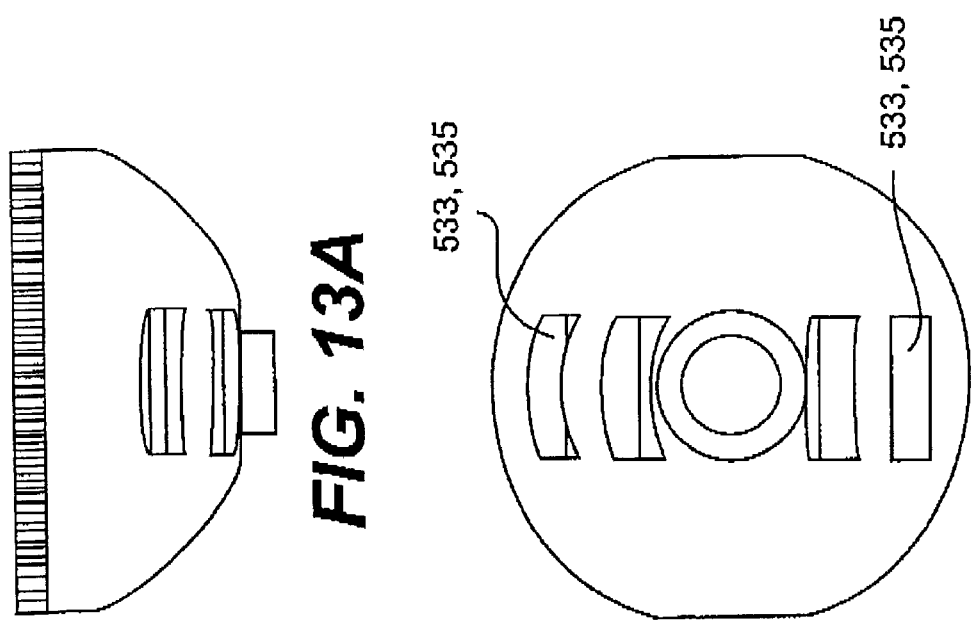
FIG. 13A
FIG. 13B

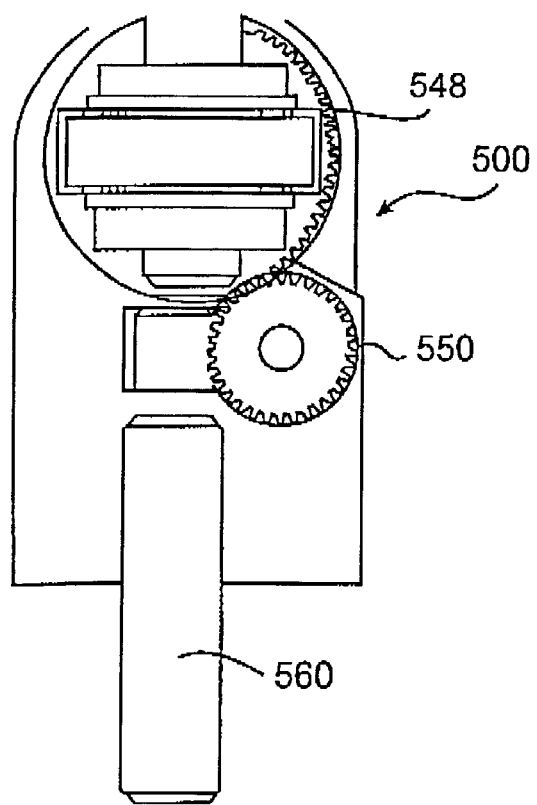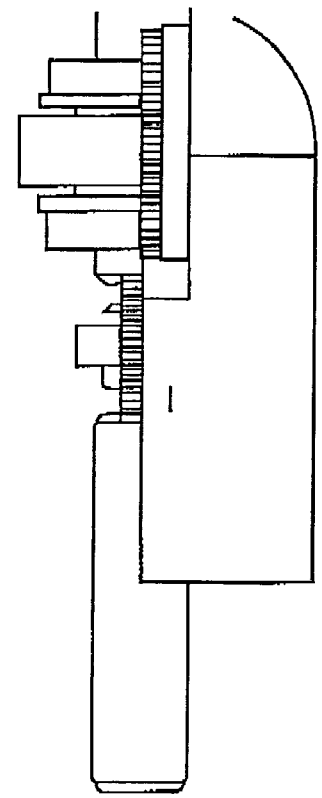
FIG. 14A
FIG. 14B
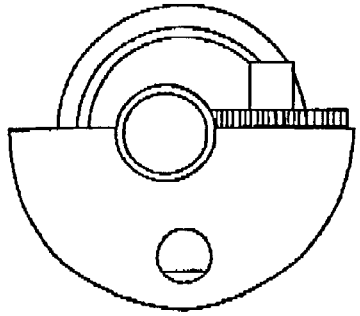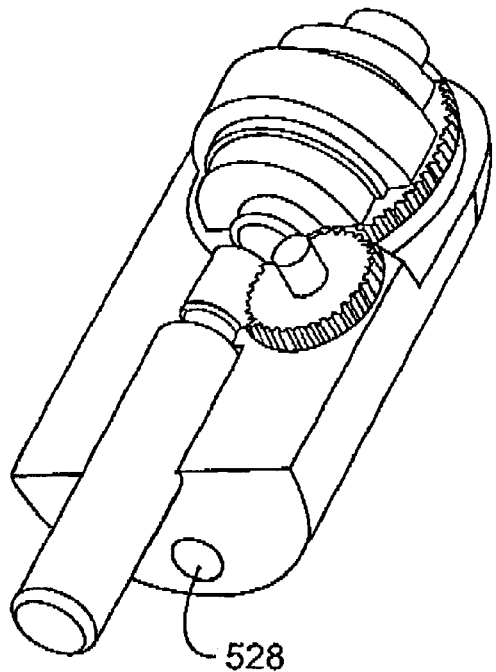
FIG. 14C
FIG. 14D

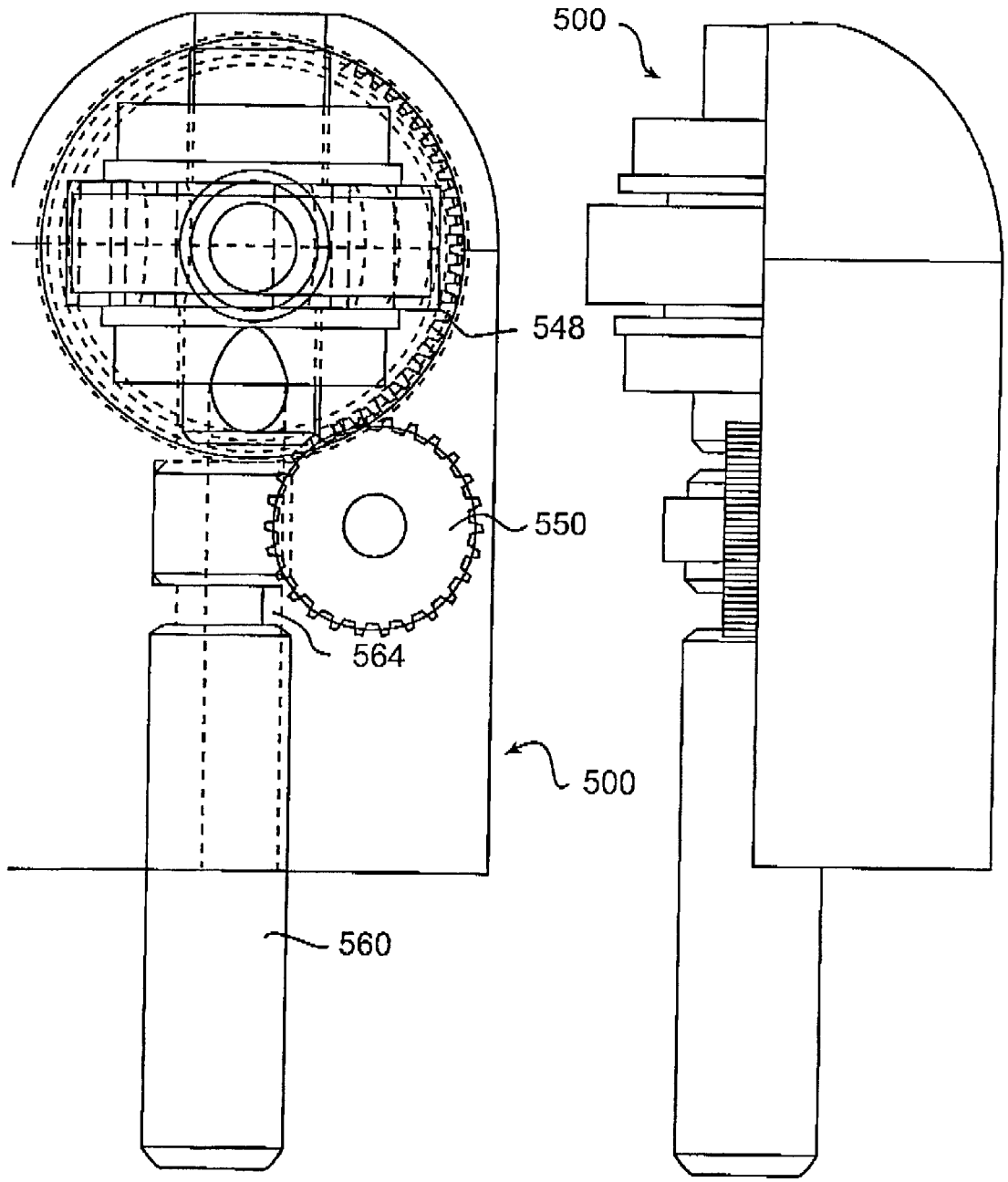
FIG. 15A  FIG. 15B

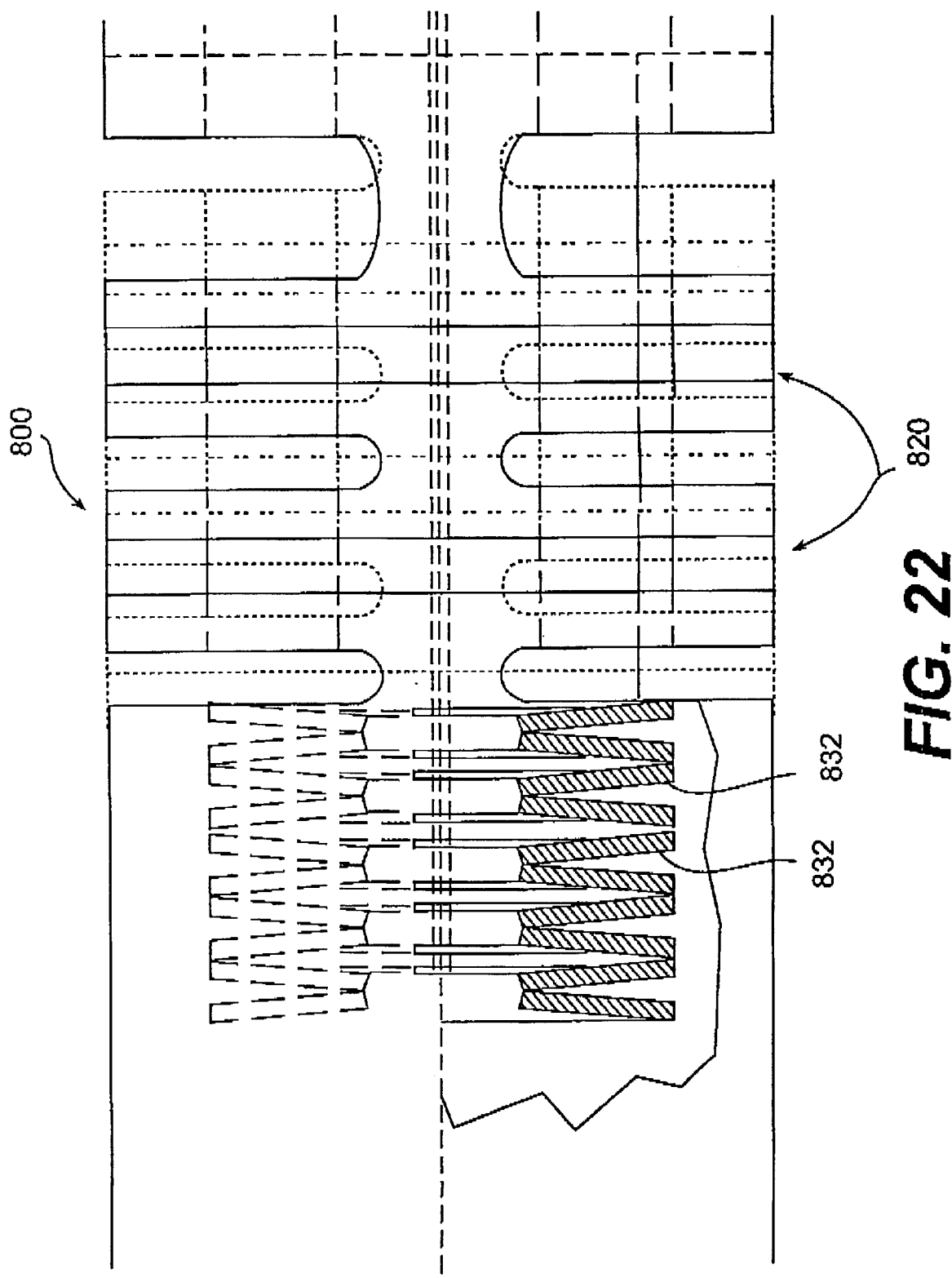

BONE CUTTING AND BREAKING APPARATUS, AND MINIATURIZED CUTTING HEAD

This is a division of application Ser. No. 09/377,403, filed Aug. 20, 1999 now U.S. Pat No. 6,309,394, and claims the benefit of U.S. provisional application No. 60/097,332, filed Aug. 20, 1998, which is incorporated herein by reference.

BACKGROUND OF THE INVENTION

1. Field of the Invention

The present invention relates to apparatus used in the cutting and breaking of bones in certain medical procedures.

2. Description of the Related Art

Certain medical procedures require the surgeon to break a bone. Examples of these procedures are bone lengthening operations that require the insertion of a bone lengthening device or other prosthesis. The conventional manner of performing this operation usually requires removing the bone marrow in the center of the bone by drilling through one end of the bone down its longitudinal axis to create a cavity in the bone marrow in which the bone lengthening nail or prosthesis is to be fit.

After this cavity has been drilled, holes are generally drilled perpendicular to the bone at the site where the bone is to be broken. Once the holes are drilled, a chisel is inserted into this region and driven through the bone section and twisted to cause the bone section to break.

The bone lengthening nail is then inserted into the cavity so that the upper portion is lodged in one-half of the broken bone and the lower portion of the nail is lodged in the lower portion of the broken bone. The nail is periodically lengthened in order to lengthen the bone, which heals itself through a knitting process. This bone breaking procedure is an excessively invasive procedure, requiring drilling the holes in the bone and inserting the chisel blade to actually create the fracture.

Moreover, fractures made by this procedure tend to be irregular and fragmented, making the bone more difficult to realign once the bone lengthening device is inserted into the bone marrow cavity.

Thus, there is a need for a bone breaking apparatus that will provide an internally-created cut or stress concentration so that the resulting bone break is regular and easy to realign once a bone lengthening device is inserted into the cavity.

In an alternative procedure, a bone saw is placed within the bone marrow cavity and the bone cut radially from within. However, the cutting depth cannot be controlled so that the depth of the cut can vary according to the thickness of the bone. Therefore, a single cut of uniform depth is made, where the depth of the cut is limited by the thinnest portion of the bone in order to prevent damaging the periosteum and surrounding soft tissue at the thinnest point by cutting deeper. While the thinnest portion of the bone may be cut completely through, there are other areas which are only partially cut. Additionally, this type of saw is incapable of cutting the bone along its length.

Further, such bone saws cannot be used for cutting the femur head due to their large size and limited angular motion. In particular, features such as air inlet and exhaust hoses limit the angle to which the cutter head can be moved.

SUMMARY OF THE INVENTION

To overcome the disadvantages of the prior art, and in accordance with the purposes of the invention, as embodied and broadly described in the application, the invention provides a method of cutting a bone using a bone cutting apparatus. The method includes determining a first cutting depth based on variations in radial bone thickness of the bone, inserting a bone cutting apparatus having a cutting blade into a hollow space within the bone, moving the cutting blade radially to set it to the first cutting depth, cutting the bone at the first cutting depth, determining a second cutting depth based on variations in the radial bone thickness, adjusting the cutting blade radially to set it to the second cutting depth, and cutting the bone at the second cutting depth.

According to another aspect of the present invention, a bone cutting apparatus is provided. The bone cutting apparatus includes a power source, an articulating cutting assembly connected to the power source and having a cutting blade, the cutting blade moveable between a stored position and a cutting position, a cutting guide for guiding the cutting blade during bone cutting; and means for locking the bone cutting apparatus to a bone being cut, wherein at least a portion of the bone cutting apparatus including the cutting assembly is shaped to fit within a cylindrical cavity of a bone.

According to another aspect of the present invention, a powered bone breaking mechanism is provided, comprising a machine spring, a powered spring having a compacted state and an expanded state, the powered spring comprising a shape memory alloy, and a power source connected to the powered spring.

According to one aspect of the present invention, a method of breaking a weakened bone is provided. The method includes attaching a powered bone breaking apparatus to a weakened bone, and moving a powered spring of the apparatus from a compacted state to an expanded state.

According to a further aspect of the present invention, a miniature cutting device is provided. The miniature cutting device comprises a turbine and burr, a spherical turbine support housing, including two hemispherical turbine support housing portions, wherein the turbine support housing portions fit together to form the spherical turbine support housing and to hold the turbine and burr, and wherein a first hemispherical turbine support housing portion includes slots for directing air onto blades of the turbine to rotate the turbine, two outer cutter assembly support housing portions, wherein each hemispherical turbine support housing portion is fitted to a respective outer cutter assembly support housing portion, wherein the outer cutter assembly support housing portion fitted to the first hemispherical turbine support housing includes an air inlet passage for supplying pressurized air to the slots of the first hemispherical turbine support housing, and means for rotating the turbine and burr about a longitudinal axis of the device.

According to yet another aspect of the present invention, a method of removing an interior portion of a femur head is provided. The method comprises creating a small incision into skin below a hip of a patient to expose the femur, drilling a small hole into the femur, inserting a miniaturized femur cutter into the hole in the femur, rotating a turbine and burr of the miniaturized femur cutter at a high speed to cut away a rotting, decayed, or cancerous section of the femur head, changing the cutting angle as necessary by rotating the turbine and burr about a longitudinal axis of the miniaturized femur cutter, and removing the miniaturized femur cutter from the femur.

Additional features and advantages of the invention will be set forth in the description that follows, and in part will be apparent from the description, or may be learned by practice of the invention. The objectives and other advantages of the invention will be realized and attained by the system particularly pointed out in the written description and claims hereof, as well as the appended drawings.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings:

FIG. 5 is an exploded isometric view of a second embodiment of a cutting assembly of the present invention;

FIGS. 6A–6C are side, front, and top views, respectively, of an embodiment of a guide mechanism of the present invention

FIGS. 13A–13D are various views of a hemispherical turbine housing of the miniaturized femur head cutter;

FIGS. 14A–14D are various views of the miniaturized femur head cutter with one cutter support housing and one hemispherical turbine support housing removed;

FIGS. 15A and 15B are enlarged views of FIGS. 14A and 14B, respectively;

FIG. 22 is a side view of the bone breaking device of FIG. 21 in an expanded state.

DESCRIPTION OF THE PREFERRED EMBODIMENTS

Reference will now be made in detail to the present preferred embodiments of the present invention, examples of which are illustrated in the accompanying drawings.

The bone cutting apparatus of this invention is designed to provide a cutting blade that is capable of radial movement, circumferential movement, and movement along the longitudinal axis of the bone being cut. The cutting blade is intended to be capable of varying the depth of a cut around the circumference of the bone as necessary in order to cut through the bone preferably in the form of a "Z" shaped cut, such that the blade has passes through the thickness of the bone at selected locations and breaches the outer circumference of the bone. That is, the "Z" cut bone cutting device is designed to provide a guided means for cutting a section of bone from inside a cavity created by removal of bone marrow within the bone through the outer circumference of the bone, allowing the bone to be easily broken in preparation for a lengthening procedure.

Figure 1:
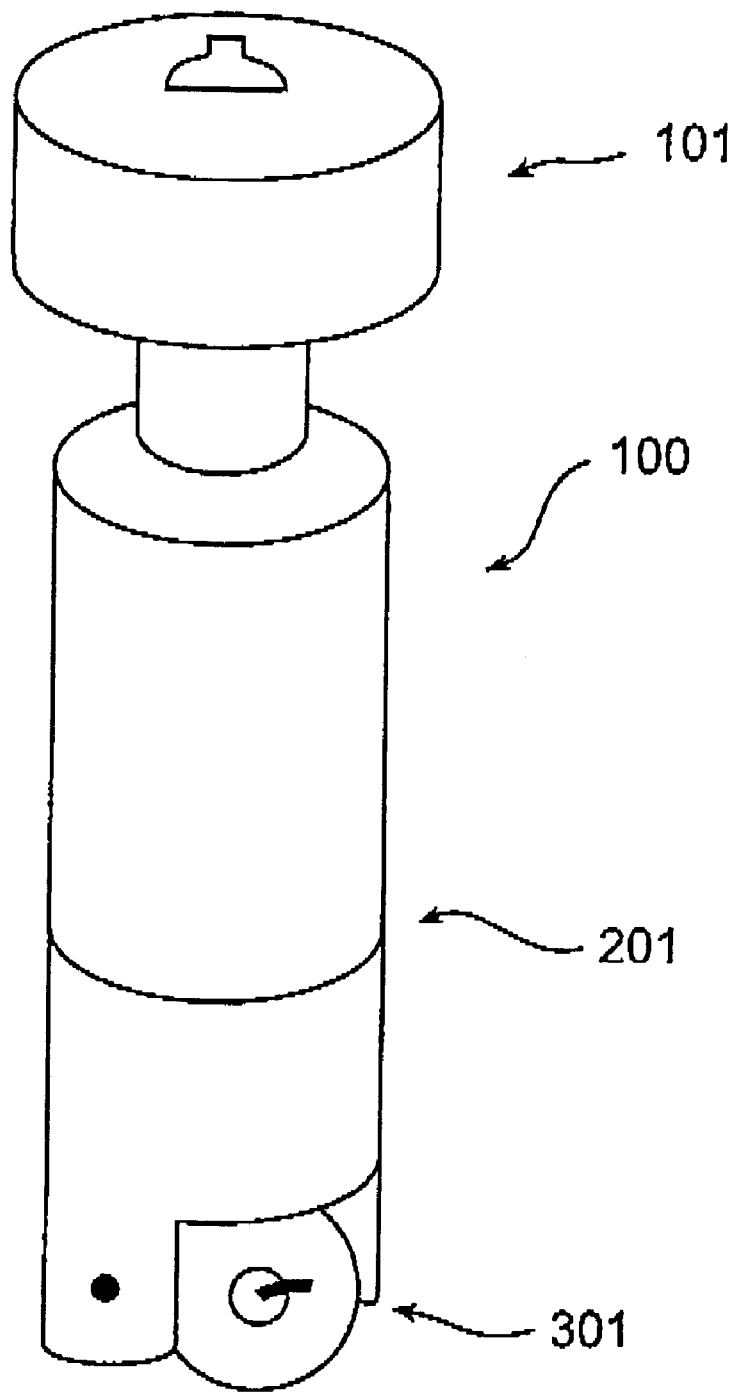
FIG. 1 is an isometric view of the bone cutting device of the present invention.

According to one aspect of the invention, and as embodied in FIG. 1, a bone cutting device 100 is provided and includes an upper body portion, a lower body support portion, and a cutting assembly. As shown in FIG. 1, upper body portion 101 may include actuating means for actuating the cutting assembly and handle means. Lower body portion 201 may include guide means for guiding the cut made by the cutting assembly, and means for supporting the device on the surgical site. Cutting assembly 301 may include a power source and a cutting tool.

According to one aspect of the invention, the bone cutting device includes an upper body portion 101. As embodied herein and shown in FIGS. 1, 2A, 2B, and 4, upper body portion 101 of bone cutting device 100 may include handle means 110. Handle means 110 may be formed of metal, or any other suitable material which is capable of being sterilized so as to be surgically reusable. Alternatively, handle means 110 may be made of a disposable material, such as a plastic, and be intended for a single use only. Handle means 110 is designed for the surgeon to grasp and manipulate during the surgical procedure, thereby guiding and controlling the cutting of the bone.

Figure 4:
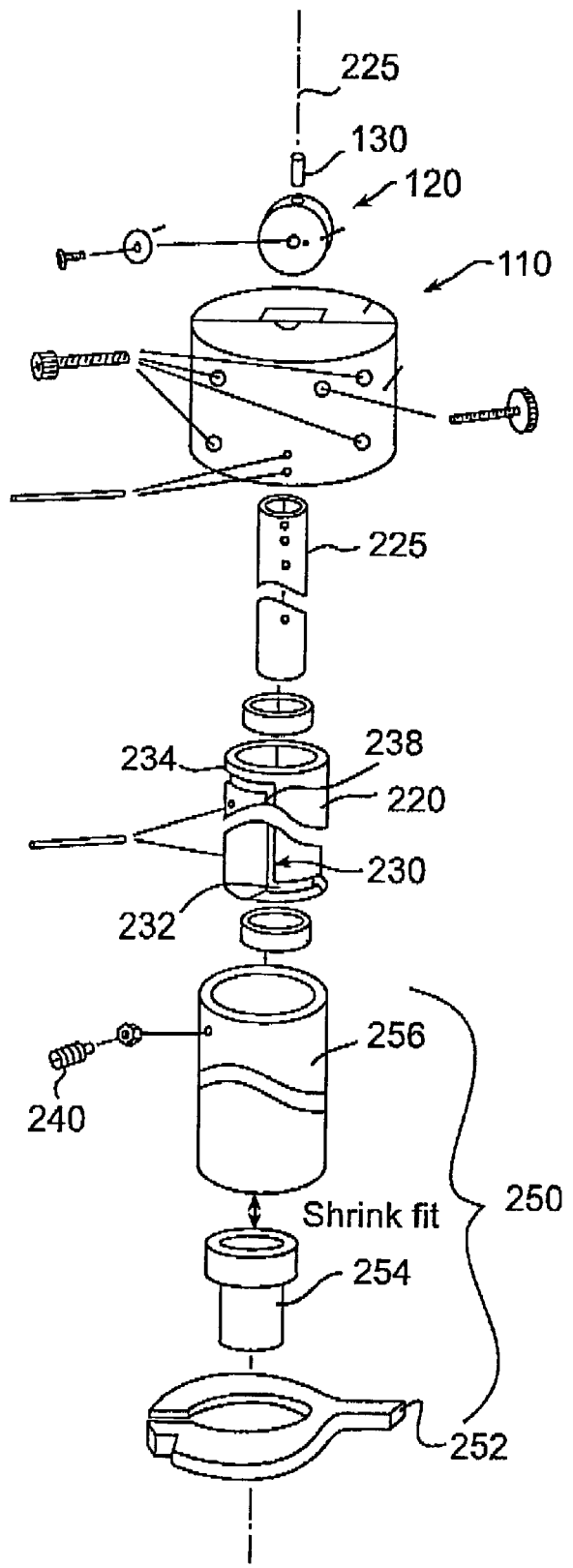
FIG. 4 is an isometric view of the body of the bone cutting device of the first embodiment of the present invention.

Upper body portion 101 of bone cutting device 100 may also include actuating means 120 for actuating a cutting assembly 301 of the bone cutting device 100. As embodied herein and shown in FIG. 4, the actuating means 120 may include a thumb actuatable, pivoting projection 130. Projection 130 is connected to the cutting assembly 301 such that movement of projection 130 causes a cutting tool of the present invention to move between a position close to being parallel to a longitudinal axis 140 of the bone cutting device, a storage position, and a position perpendicular to the longitudinal axis 140 of the bone cutting device, an in-use position. As shown in FIG. 4, projection 130 may include a pulley lever attached to a pulley wheel. Projection 130 may be made of any material suitable for sterilizing for medical use, such as stainless steel, titanium, or various polymers. Alternatively, projection 130 may be a button, a on/off switch, etc.

According to one aspect of the invention, the bone cutting device 100 includes an lower body portion 201. As embodied herein and shown in FIGS. 4, 6, and 7, lower body portion 201 of bone cutting device 100 may include a guide means for guiding the cutting of the bone. The guide means may include a cutting guide 220, as shown in FIGS. 4, 6, and 7, pictured as a tube or cylinder which circumferentially surrounds a portion of a central main shaft 225 of the bone cutting device 100. Cutting guide 220 has a slot or groove 230 which is in the shape of the cut to be made in the bone being cut. The guide means may also include a pin 240 which acts as a groove follower pin, moving within and following the slot or groove 230 in cutting guide 220 to control the direction of the cutting and thereby the shape of the cut made.

Figure 7C:
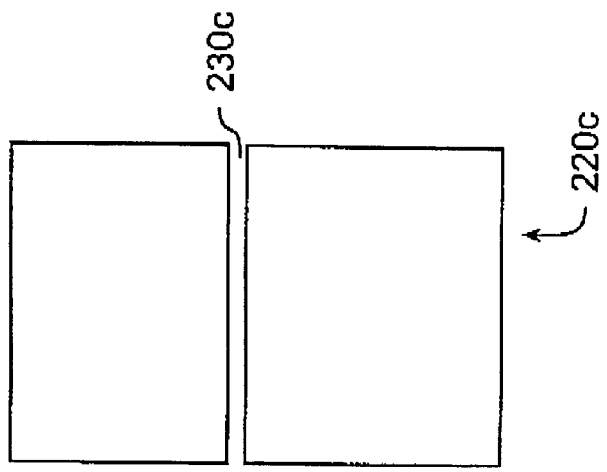
FIGS. 7A–7C are side views of alternative embodiments of a cutter guide of the present invention.
Figure 7B:
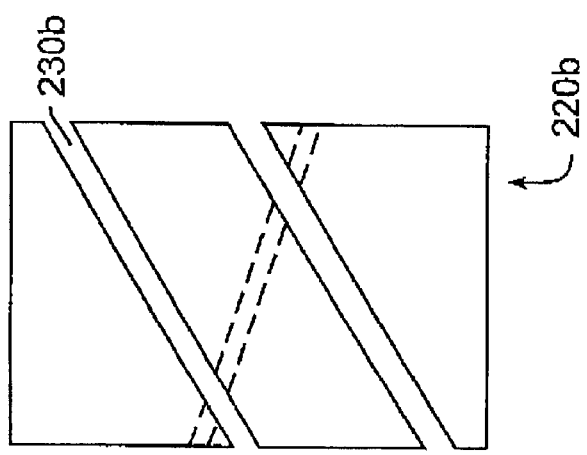
Figure 7A:
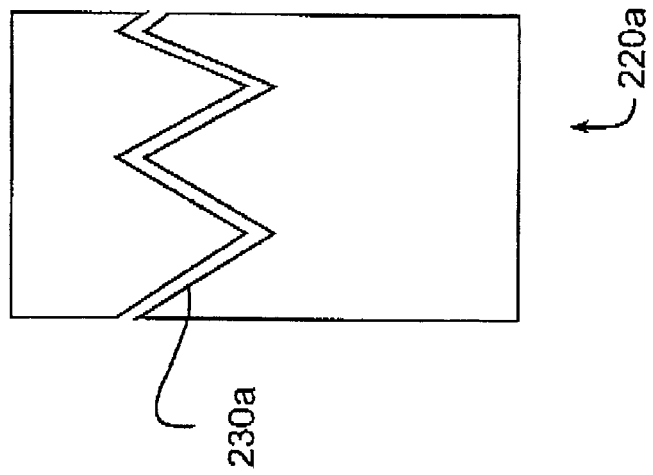

In the presently preferred embodiment, groove 230 is shaped to create a "Z" cut which will be explained in more detail further on. In order to create the "Z" cut, groove 230 is formed in the shape of the "Z" to be cut into the bone. Thus, groove 230 has two semi-circular groove portions 232, 234, which are diametrically opposed to one another, located on opposite sides of cutting guide 220 and are distanced vertically from one another and connected to each other by two longitudinal groove portions 236, 238. It may be desirable to create a cut in a shape other than a "Z," and for such a different cut, a different cutting guide 220a, 220b, 220c with a differently shaped groove 230a, 230b, 230c may be provided as shown in FIGS. 7A, 7B, and 7C. In each instance, cutting guide 220a, 220b, 220c includes a groove 230a, 230b, 230c formed into the shape of the desired cut in which a pin 240 will sit and follow to ensure that the bone is cut in the desired shape. Examples of other types of desirable shapes for cuts include a radial cut which would use a circular groove, a longitudinal cut which would include a longitudinal groove, and a spiral cut which would use a spiral groove.

Cutting guide 220 is constructed to be removable from bone cutting device 101, and to be interchangeable with differently sized and shaped guides and with guides having differently shaped grooves for allowing differently shaped cuts. Cutting guide 220 must be of a material that is sterilizable, and sturdy enough to withstand any pressure applied by pin 240 in groove 230. Stainless steel and titanium are examples of a suitable material.

Groove 230 may be a slot which extends completely through a width of cutting guide 220, or it may be a deep or a shallow groove, dependent upon the type of pin used as follower pin 240. Alternatively, groove 230 may consist of a raised portion or portions on cutting guide 220 which pin 240 can follow.

The guiding means may also include a brace assembly 250. Brace assembly 250 is placed over main shaft 225 and cutting guide 220, and is located between a cutting assembly support 299 and upper body portion 101 of the cutting device 100. As embodied herein and shown in FIGS. 2A, 2B, and 4, brace assembly 250 includes a brace arm 252 which is mounted above cutting assembly support 299 about shaft 225. Brace arm 252 supports the cutting device 100 and holds it in place against the bone during the actual cutting procedure. A brace bottom 254 and a brace top 256 fit over shaft 225 above brace arm 252, brace bottom 254 fitting tightly into a base portion of brace top 256 in order to hold it in a desired location. Brace top 256 includes follower pin 240 extending through brace top 256 to sit within slot or groove 230 of cutting guide 220.

As with other portions of the bone cutting device 100, brace assembly 250 should be sterilizable so as to allow it to be reusable in surgical procedures. In a preferred embodiment, brace assembly 250 is made from stainless steel, but many other materials would be suitable as would be obvious to one of ordinary skill in the art.

Brace assembly 250 is connected to main shaft 225 and moveable with respect to shaft 225 with cutting guide 220. In use, the surgeon manipulates brace assembly 250, causing pin 240 to follow the groove in cutting guide 220, and thus controls the directional movement of the cutting tool as discussed in greater detail later.

According to one aspect of the invention, the bone cutting device 100 includes a cutting assembly 301. As embodied in FIGS. 2A, 2B, 3, and 5, cutting assembly 301 may include a power source for powering a cutting tool. Although any suitably sized motor can be used, as well as other sources of power, the preferred embodiment utilizes an air turbine 302, which minimizes the parts that are actually required to be kept in a cutting assembly 301 of the device. A cutting tool 304, herein embodied as a burr, is rotated by the turbine 302 which is housed in the cutting assembly 301 in a turbine housing 306. Air is supplied to turbine 302 through flexible tubes 322 that extend from the cutting assembly 301 to a source of air external from the bone cutting apparatus 100. Additional flexible tubes 323 may be used to provide physiologic solution (such as saline solution) to the cutting site to wash away debris and keep the cutting site and cutting tool cool. Turbine 302 provides sufficient torque to cutter 304 such that cutter 304 penetrates the hard material of the bone during use.

Figure 3:
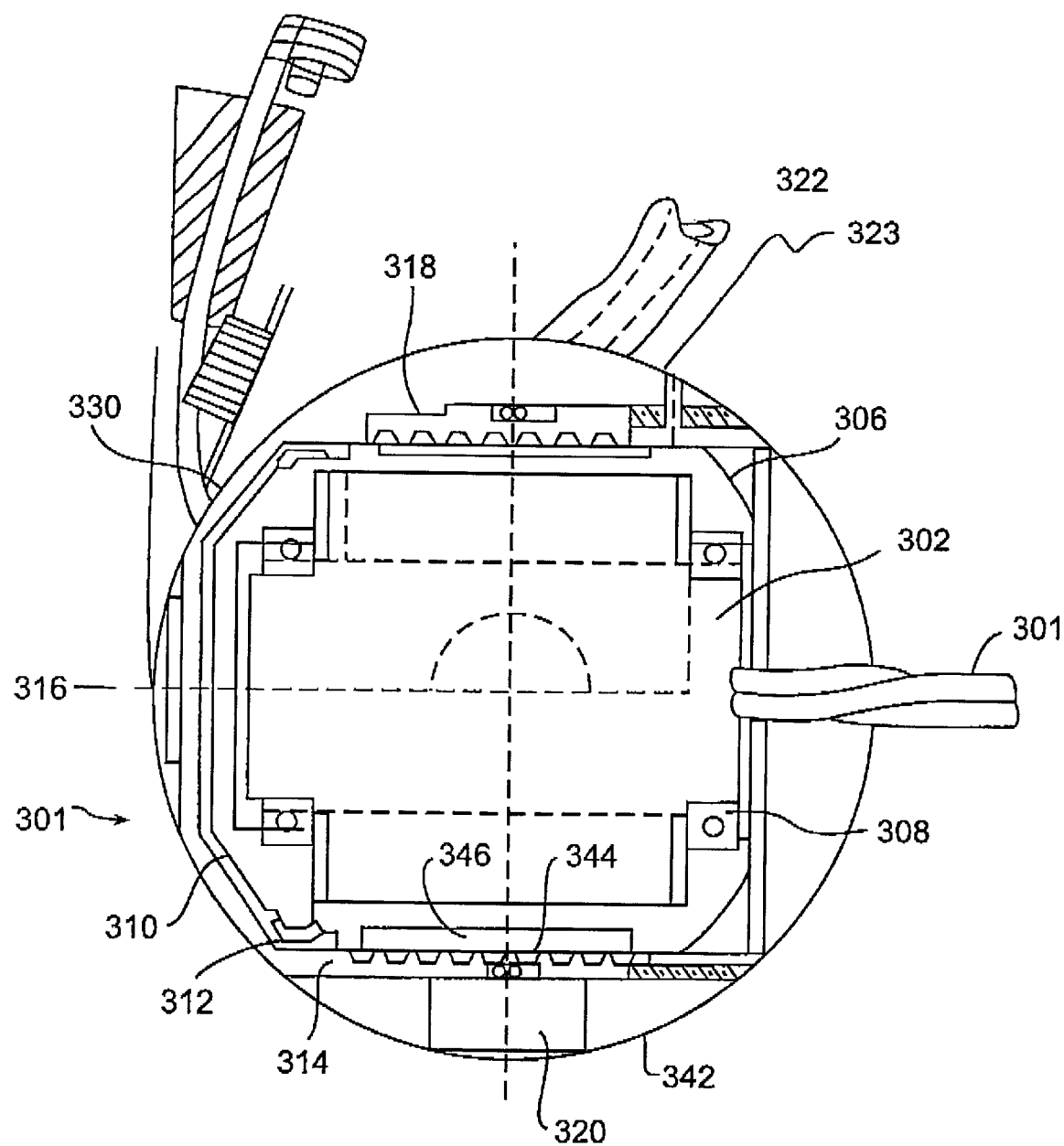
FIG. 3 is a cross-sectional view of a first embodiment of a cutting assembly of the present invention.

In a first embodiment shown in FIG. 3, air turbine 302 with integral burr 304 is mounted in turbine housing 306 by a pair of bearings 308. A housing end cap 310 is secured to turbine housing 306 via clamp ring 312 and precisely locates air turbine 302 within turbine housing 306. A pivot housing 314 includes a bore shaped to slidingly receive turbine housing 306, and turbine housing 306 is guided to move in a longitudinal direction along an axis 316 coincident with the centerline of the burr 304, by a feed rack 318 which acts as a key for the interface between turbine housing 306 and pivot housing 314. As embodied in FIG. 3, there are two feed racks 318 diametrically opposed to one another and lying in a plane perpendicular to the axis of a pivot axle 320. Flexible air lines 322 are attached to pivot housing 314, and pivot housing 314 includes suitable air passages to direct flow of air through corresponding passages in turbine housing 306 and into and out of the blades of air turbine 302.

Figure 8:
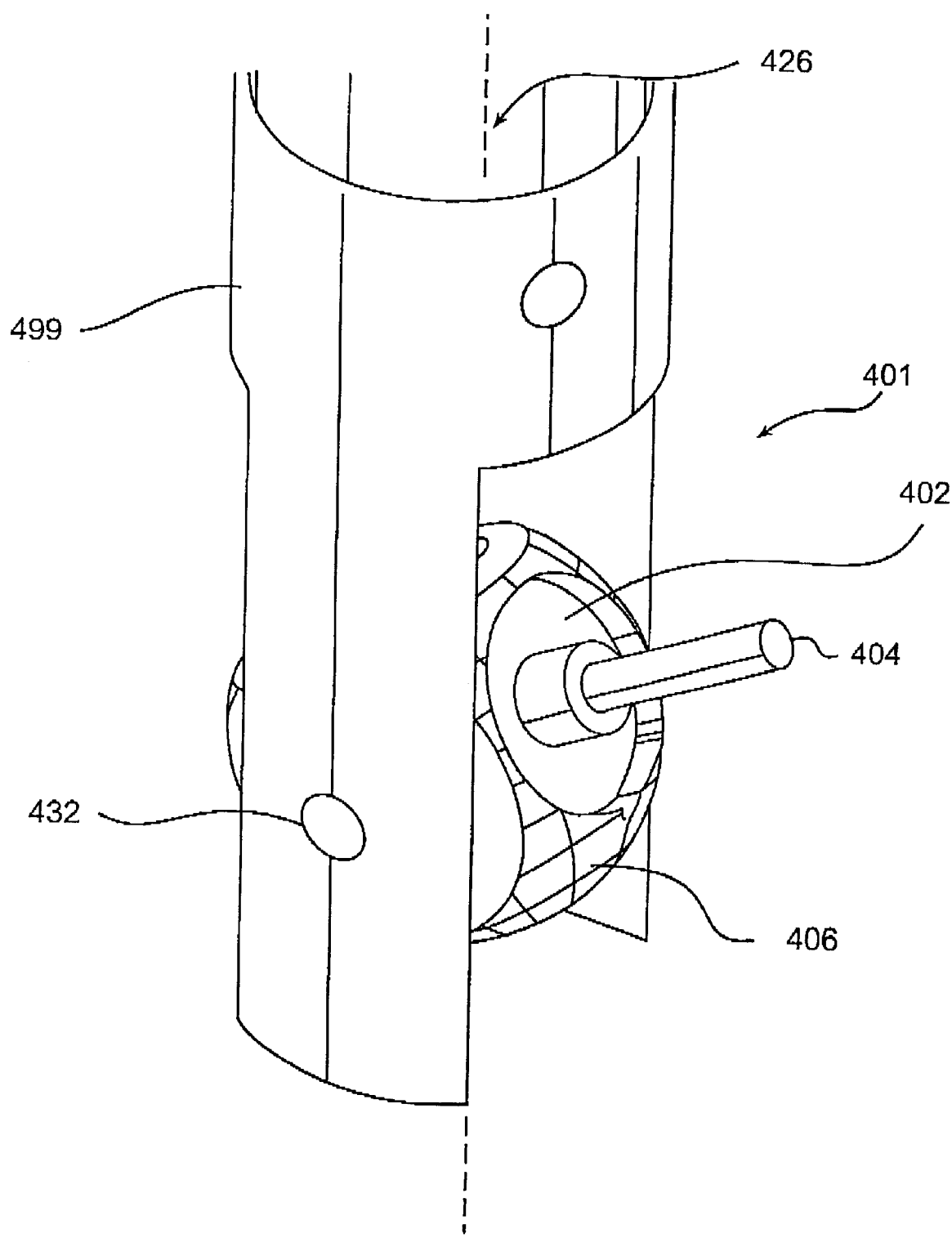
FIG. 8 is an isometric view of the second embodiment of the cutting assembly of the present invention shown in FIG. 5.
Figure 9A:
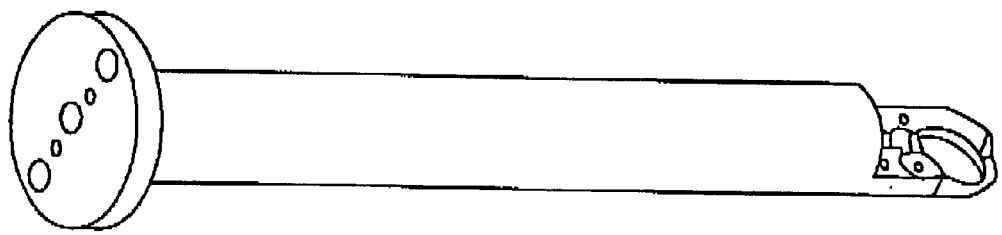
FIGS. 9A and 9B are isometric and top views, respectively, of a miniaturized femur head cutter of the present invention.
Figure 9B:
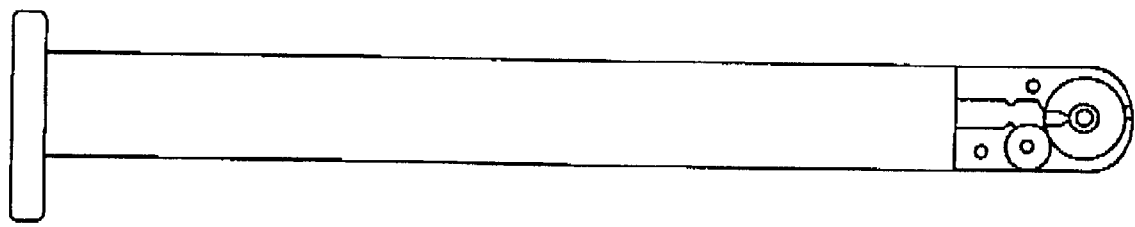

According to another, more preferred embodiment of the present invention shown in FIGS. 5 and 8, in which similar numerals designate similar components, a bone cutting apparatus includes a turbine 402 and a burr 404 which are fixed in turbine housing 406 by a turbine locking screw 430. The turbine housing 406 preferably is mounted within a cutting assembly support 499 by a pair of pivot pins 432. This construction allows turbine housing 406, and therefore turbine 402 and burr 404, to freely rotate between positions located at 0 degrees, where burr 404 extends horizontally from the device and is perpendicular to the main shaft 425 of the device, and a position approaching 90 degrees, where burr 404 is not extended but remains locked in an upright, near vertical position adjacent to the main shaft 425 of the device (the stored position). By use of a locking mechanism to be discussed later, cutting assembly 401 can be fixed in any position from 0 degrees to the stowed position angle approaching 90 degrees. Thus, the depth of the cut made in the bone, which is directly related to the angle of the burr, can be controlled and varied as the surgeon desires.

The cutting assembly 301, 401 is capable of rotating about the longitudinal axis 226, 426 of the device, which coincides with the longitudinal axis of the cavity in the bone so that the burr 304, 404 can circumferentially cut into the inner surface of the bone. Burr 304, 404 is also mounted in such a way that it can move radially to progressively penetrate into the bone from the interior surface to the exterior surface thereof. This radial movement must be highly controlled in order to ensure that the cutter cuts only the bone and not the surrounding flesh. Cutting assembly 301, 401 is mounted to a cutting assembly support 299, 499 which provides bearing support for articulation and controlled motion of cutting burr 304, 404.

The preferred type of cut will be referred to as a "Z" cut for its appearance in cross-section. The "Z" cut is generally formed in the following manner. First, a surgeon inserts the cutting blade (burr 304, 404) into the bone from the interior section thereof, and the cutting assembly 301, 401 is rotated about the longitudinal axis 226, 426 of the device from the 0° position to the 180° position while the cutter 304, 404 is cutting through the bone. This creates a semicircular cut in one transverse plane of the bone. The cutting assembly 301, 401 is then caused to move along the longitudinal axis of the bone a set distance. Once this set distance is reached, the cutting assembly 301, 401 is again rotated about the longitudinal axis 226, 426 from the 180° position to the 360° or 0° position forming another semicircular cut in another transverse plane of the bone, which is off-set from the first plane by the distance moved along the longitudinal axis. The cutting assembly 301, 401 is then longitudinally returned to its original cutting position, thereby completing the Z cut in the bone. The cutting process, using the first embodiment, follows a specific sequence as discussed below with respect to FIGS. 1, 2A, 2B, 3, and 4.

Figures 2A, 2B:
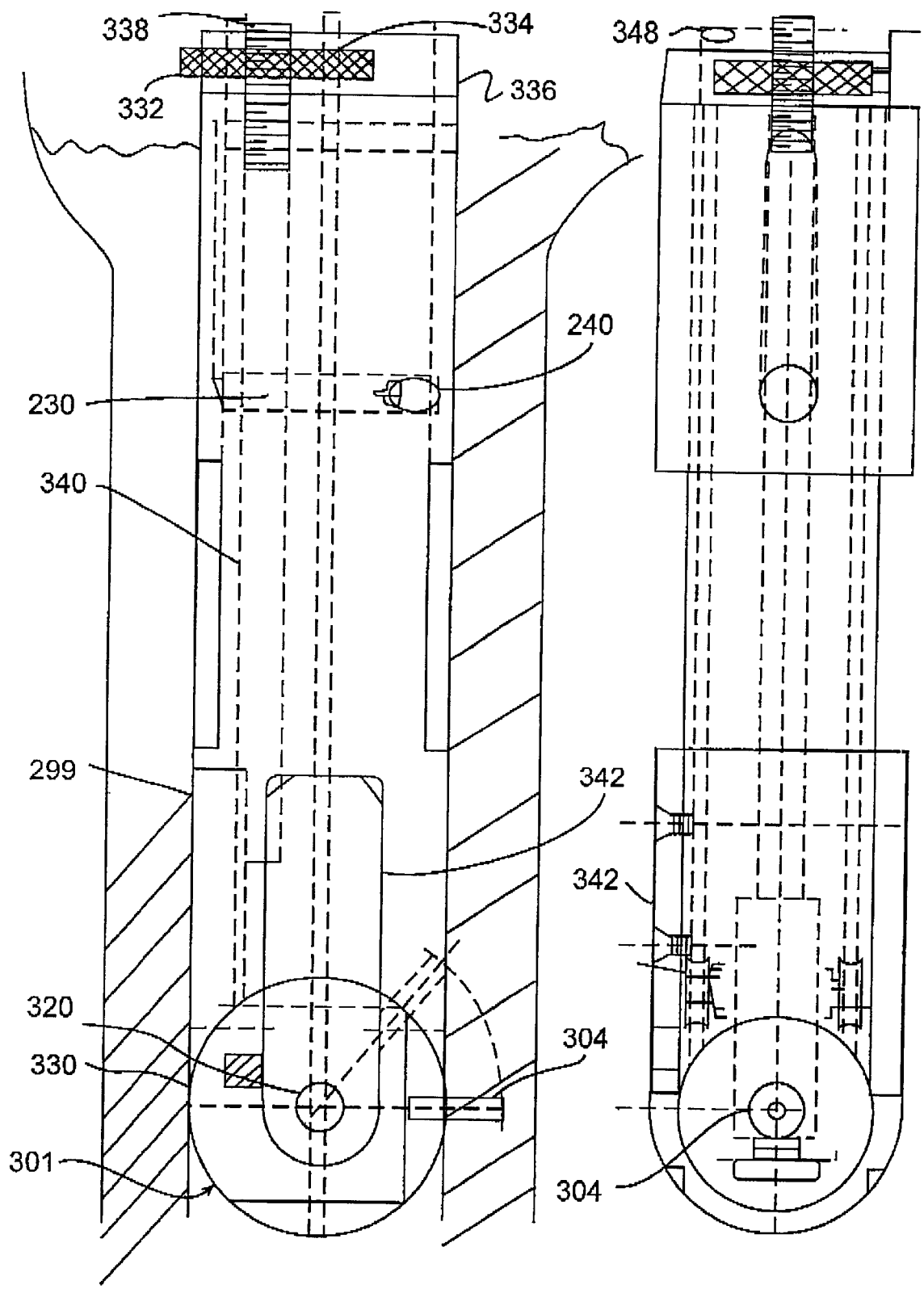
FIGS. 2A and 2B are a cross-sectional views of a first embodiment of the bone cutting device of the present invention.

First, the cutting assembly 301 with cutter 304 in its stowed position, shown in phantom in FIG. 2B, is inserted into the bone marrow cavity and cutting guide 220 is secured in place within the cavity.

The cutting blade (burr) 304 can be moved into its cutting position by the provision of a pivot drive blade 330, which is fixed at one end of the pivot housing 314 and can thus pivot the cutting assembly 301 by being extended and withdrawn by a pivot adjustment nut 332 located at the upper portion 101 of the bone cutting device 100. Since the pivot adjustment nut 332 is trapped in a slot 334 in a thrust collar 336 located on the upper portion of the bone cutting apparatus, the reaction of the pivot adjustment nut 332 on the pivot drive threads 338 on the pivot drive rod 340 causes the articulating cutting assembly 301 to rotate until the rotation is forced to stop by contact of the side surface of a pivot bearing block 342. Air is caused to flow through the flexible air lines 322, thereby causing cutter 304 to turn at high speed in preparation for cutting. During rotation the cutter 304 is continuously turning and cuts a radial slot in the material of the bone.

The radial movement of the cutting assembly 301 may be provided by the provision of feed racks 318 that are contained in the cutting assembly 301 and along the radial axis 323 of the cutter housing 306. Feed rack 318 may be actuated by a drive cable or pivot drive blade 330, located at the top of the cutting head support 299, which applies tension to a feed nut drive cable 344, which forces an adjustment nut 332 to react against feed rack 318, thereby forcing the turbine housing 306, turbine 302, and integral cutter burr 304 to move radially outward to cut additional thickness of the bone.

If pre-surgical information about the bone cross-section at this cut location dictates that cutter 304 should be projected radially outward an additional amount, a partial rotation of a feed adjustment nut 346 is made. This is done by rotating a cable drive adjuster 348 located at the top of cutter head support 299 which applies tension to feed nut drive cable 344. This rotation causes feed adjustment nut 346 to react against feed rack 318 attached to turbine housing 306, thereby forcing the turbine housing 306, its integral bearing mounted air turbine 302, and its integral cutter 304 to move radially outward to cut additional thickness of bone as the bone cross-section dictates.

The cutting action is continued by the operator as a suitable torque is applied at the upper exposed end of cutter head support 299. Cutter 304, guided by groove follower pin 240 following groove portion 232 of groove 230 in cutting guide 220, cuts a prescribed radial swath from 0 degrees to 180 degrees. As embodied herein, grooves portion 236 of groove 230 in cutting guide 220 allows the groove follower pin 240 to cut a longitudinal cut "x" inches in length in the bone in the "y" direction, after which another radial swath from 180 degrees to 360 degrees is cut as pin 240 follows groove portion 234. Finally, a last longitudinal cut "x" inches in length is made in the bone in the "−y" direction, bringing cutter 304 back to its original starting position as pin 240 follows groove portion 238 of groove 230 in cutting guide 220. Once cutting is complete, cutter 304 is retracted to its stowed position by a reverse rotation of pivot adjustment nut 332. The cutting method as outlined above assumes a priori bone thickness information is used periodically during the cutting process to adjust the radial position of cutter 304 to allow precision cutting through the bone thickness at each location, thereby completing the "Z" cut and breaking the bone.

During this rotation, the cutter has been continuously turning and has cut a radial slot in the material of the bone. In this embodiment of the invention, the slot that has just been cut is located at the 0° position of the cutting material so that the slot eventually becomes part of the Z cut in the bone.

Once the Z cut has been made in the bone, the bone cutting device 100 is withdrawn from the cavity and the bone is either already completely broken in two or requires only a minor external force to complete the cut. Alternatively, the bone can be separated by a spring actuated bone breaking mechanism as discussed below.

While this embodiment of the method of using the bone cutting device accomplishes the desired "Z" cut, there are occasions where the shortening of a limb is desired. For this reason, a new cutting guide 220a would be incorporated where smaller sections of the bone would be severed around the periphery of the bone section to be removed. One technique would be to start from the 0 degree position of the cutter 304 where the articulated cutting head 301 is caused to rotate from its stowed position to the position where the cutter 304 is perpendicular to the longitudinal axis of the cutter head support 299, and from this 0 degree position rotate the cutter 304 to +30 degrees then translate longitudinally along the bone section "y" inches, the length of the section to be removed, and to then rotate −30 degrees and then complete the severing of that section by translating longitudinally −"y" inches. This returns the cutter 304 to the 0 degree position. From 0 degrees, a swath of 60 degrees is cut through a translation cut of "y" inches followed by a −30 degrees cut to sever another section of bone. There are infinite variations to this procedure where, for example, the sections are cut leaving a sliver of supporting bone until the entire section has been cut. Thus, the final sliver can be fractured and/or cut and removed through the open bone marrow cavity.

The present invention also includes a spring actuated bone breaking mechanism. The final breaking of the bone can be accomplished by use of a spring actuated bone breaking mechanism 800, which reduces the likelihood of uneven or fragmented breaking of the bone. The spring actuated mechanism 800 of the present invention has two states, a compact state (FIG. 21) and an expanded state (FIG. 22).

Figure 21:
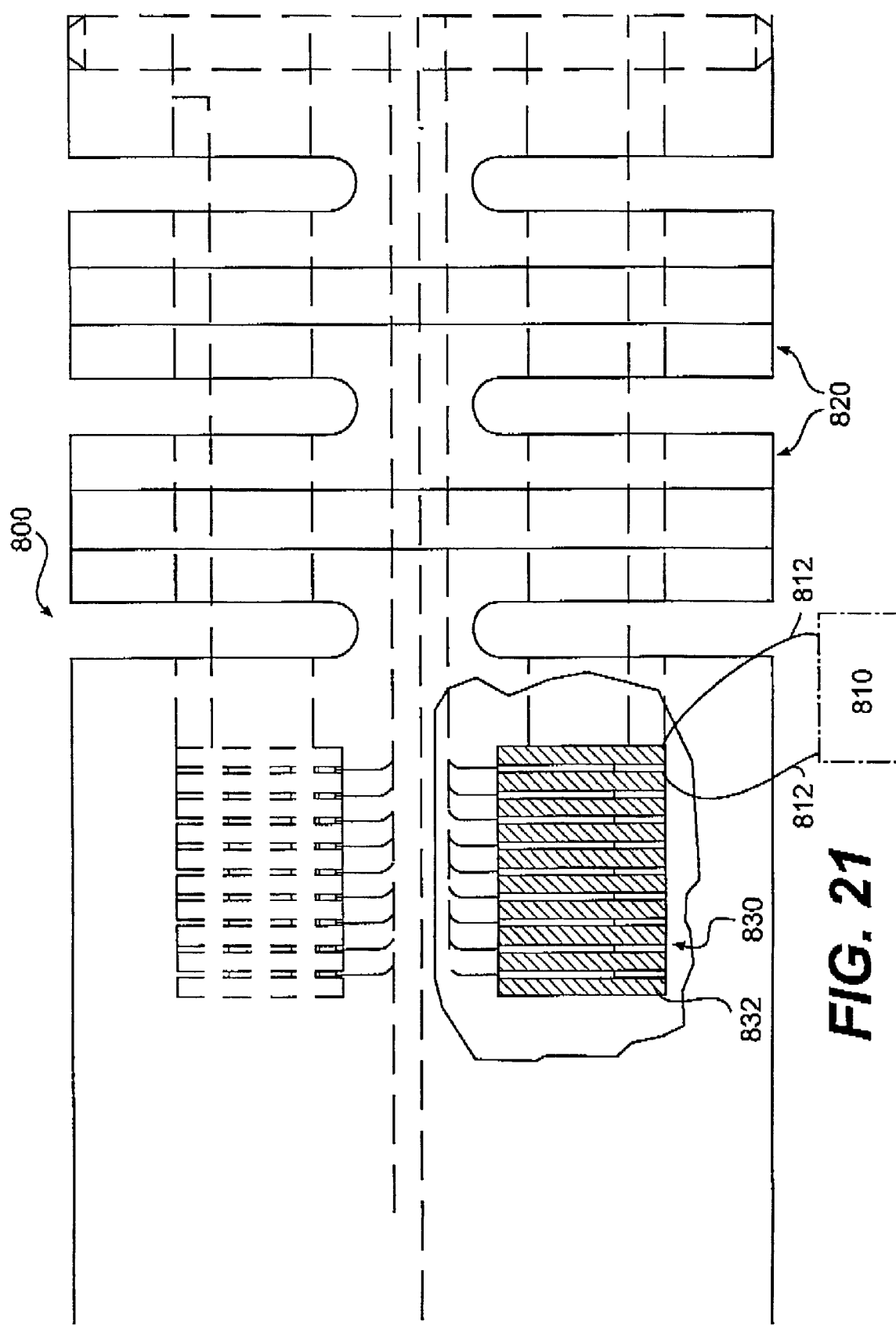
FIG. 21 is a side view of a bone breaking device of the present invention in a compacted state.

As embodied herein and shown in FIG. 21, the powered bone breaking mechanism 800 includes a machine spring 820 of a length sufficient to extend along substantial portions of both the upper and lower sections of the bone to be broken. Preferably, the spring is made from Nitinol or an equivalent phase change material. Also located inside of powered bone breaking mechanism 800 are several springs 830 comprised of a shape memory material.

A shape memory material is a material which "remembers" its original shape when energy is supplied to the material, for example, by heating. The preferred shape memory material used in this invention is Nitinol. As shown in FIG. 21, the shape memory springs 830 may include Belleville washers 832. The washers 832 are flattened out into a weakened state, and stacked atop one another to form the springs 830. The springs 830 must have sufficient strength in order to stretch the surrounding machine spring 820 which is locked to the bone at both the lower and upper portions, i.e., on either side of the weakened portion of the bone, and to overcome the breaking force of the section of the bone which has been weakened by the previously formed cut. Springs 830 are preferably connected to a source of energy which heats the springs to change from a first phase to a second phase, the second phase being a shape which extends the length of the springs. As embodied herein and shown in FIGS. 21 and 22, the spring actuated mechanism 800 can be triggered to change state via a heater circuit 810 connected to the mechanism 800. As shown, a heater resting outside the body may be attached to the spring portion via wires 812. Heat energy can be supplied to the spring formed by washers 832 by wire connection 812. When the heat is supplied, the Belleville washers assume their original expanded configuration. Alternatively, a battery may be permanently attached and encapsulated in the bone lengthening device to provide power to move the device between its compact state and its expanded state.

The upper portion of the mechanism is rigidly attached to the bone by, for example, pins extending radially through the bone and into the machine spring, and it is similarly locked in place in the lower section of the bone. When triggered, the heater circuit 810 causes two independently attached longitudinal sections of the bone breaking device to separate from one another with force sufficient to separate the longitudinal bone at the cut or weakened portion.

In yet another embodiment of the invention, a miniaturized femur head cutter may be provided. Femur head cutter 500 eliminates the air supply to turbine 302 through flexible tubes 322 of the cutting assembly of FIGS. 1–8. This allows miniaturization of the cutting head to provide a cutting tool for removal of the femur head and small enough to fit through a 10 mm hole, allowing a minimization of the invasiveness of the surgical procedure. Additionally, such a miniaturized cutting head will allow freedom to move the cutting tool through a much larger angular excursion, such as cutting a substantial portion of a full spherical surface. A larger angular excursion is desirable for machining away a femur head from inside the head. A generally hemispherical range of motion is necessary for such an action.

Figure 10:
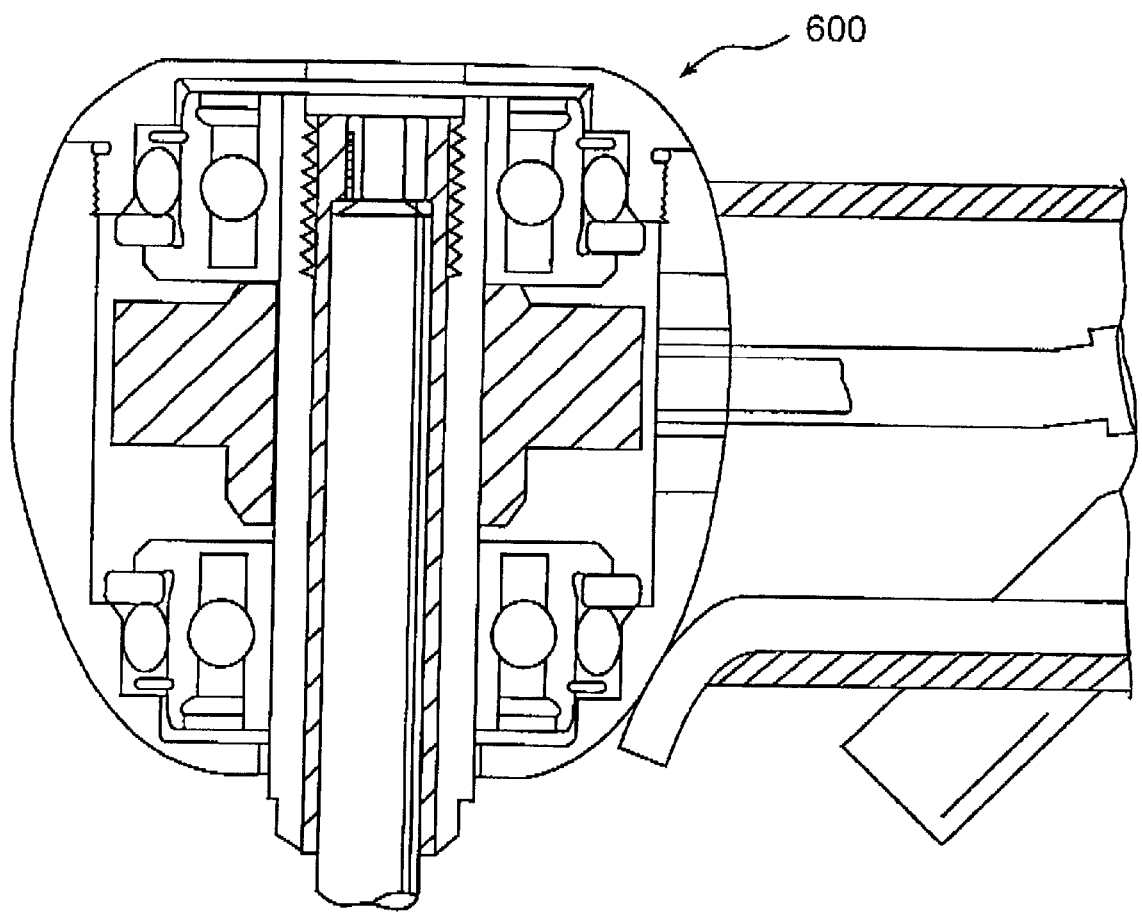
FIG. 10 is a dental drill using the turbine assembly of the cutter of FIGS. 9A–9D.
Figure 11:
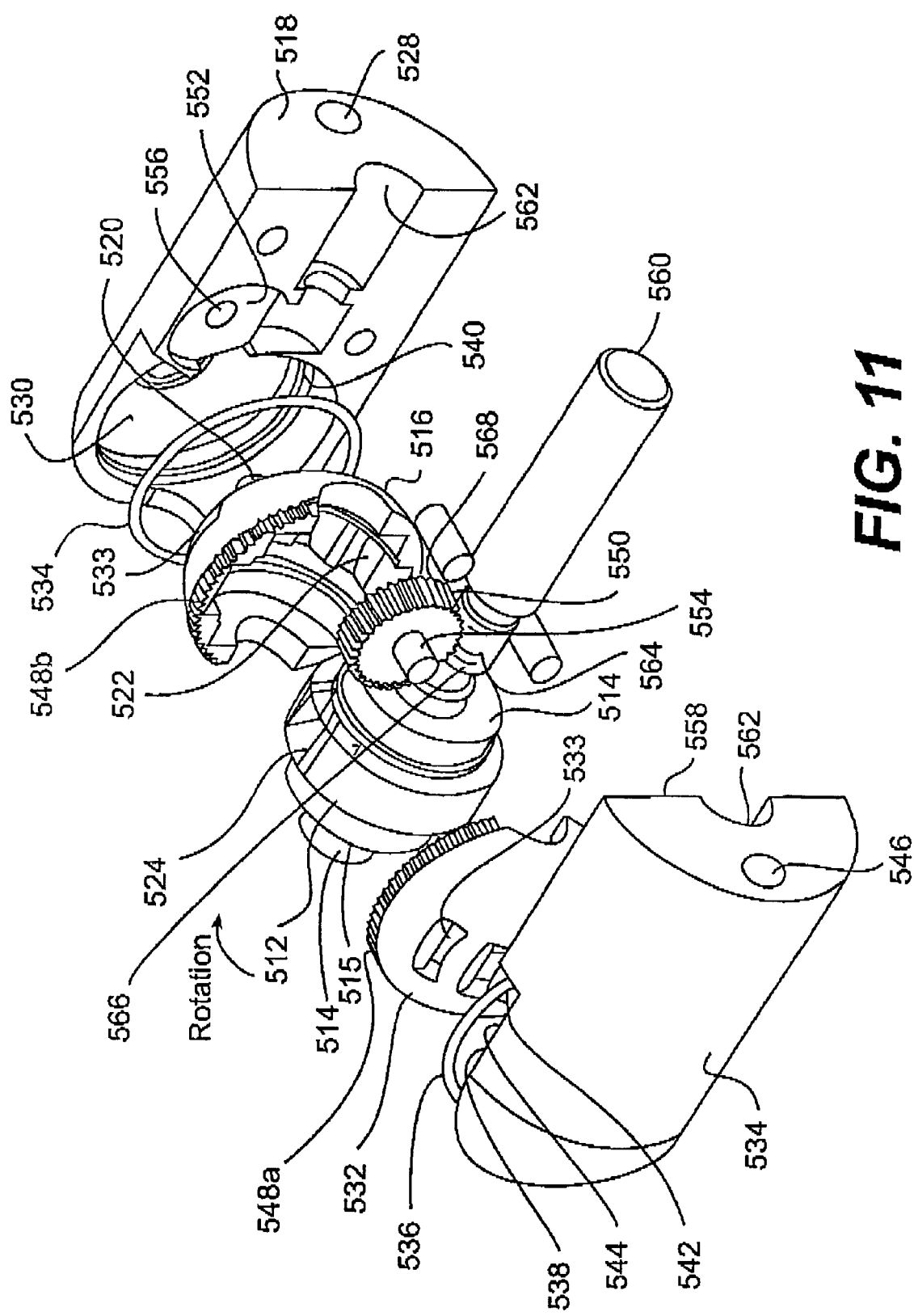
FIG. 11 is an exploded view of a cutter support housing of the miniaturized femur head cutter.

As shown in FIG. 10, such a miniaturized cutting tool is also useful to provide a dentist with a dental cutting head 600 to allow a greater range of movement for cutting and drilling at angles with respect to a support handle of the drill.

As embodied herein and shown in FIGS. 9 and 11–17D, femur cutter 500 includes a turbine 512, cutting tool 514, and support bearings 515 assembled into a hemispherical turbine support housing. The hemispherical turbine support housing includes a left half portion 532 and a right half portion 516, each of which seals against a respective o-ring 536, 534 in a respective groove 540, 542 of a respective half of an outer cutter support housing 534, 518 and pivots on an integral axle 520. Right hemispherical turbine support housing portion 516 includes a series of air directing slots 535 machined into turbine support housing portion 516 such that incoming air is directed along a path tangential to blades 524 of the turbine 512 to cause rotation of the turbine. Left hemispherical turbine support portion 532 also includes air directing slots 533 positioned to move the air along a path tangential to the turbine rotor 512. Slots 533 are cut at an angle to receive air from the turbine blades 524 and to direct it to an exhaust gas chamber 544 and then to an air outlet passage 546. The right half of the outer cutter support housing 518 includes an air inlet passage 528 which directs incoming high-pressure air into a chamber 530 within the outer cutter support housing 518.

The hemispherical turbine support housing portions 516, 532 each include an integral gear segment 548a, 548b about its periphery. When hemispherical turbine support housing portions 516, 532 are assembled with turbine 512 and bearings 515, the adjacent gear teeth of the two segments align with one another to form a single gear segment 548. Gear segment 548 engages a pinion gear 550, which is installed in a cavity 552 formed between outer cutter support housings 534, 518. Pinion gear 550 includes pivot axles 554 which fit into and pivot on bearing bores 556, 558 within the outer cutter support housings 534, 518.

An indexing shaft 560 nests between semicircular bearing seats 562 in outer cutter support housings 534, 518. The indexing shaft 560 includes a threaded portion 564 whose thread pitch 566 is compatible with the gear teeth spacing 558 of pinion gear 550.

Figure 12:
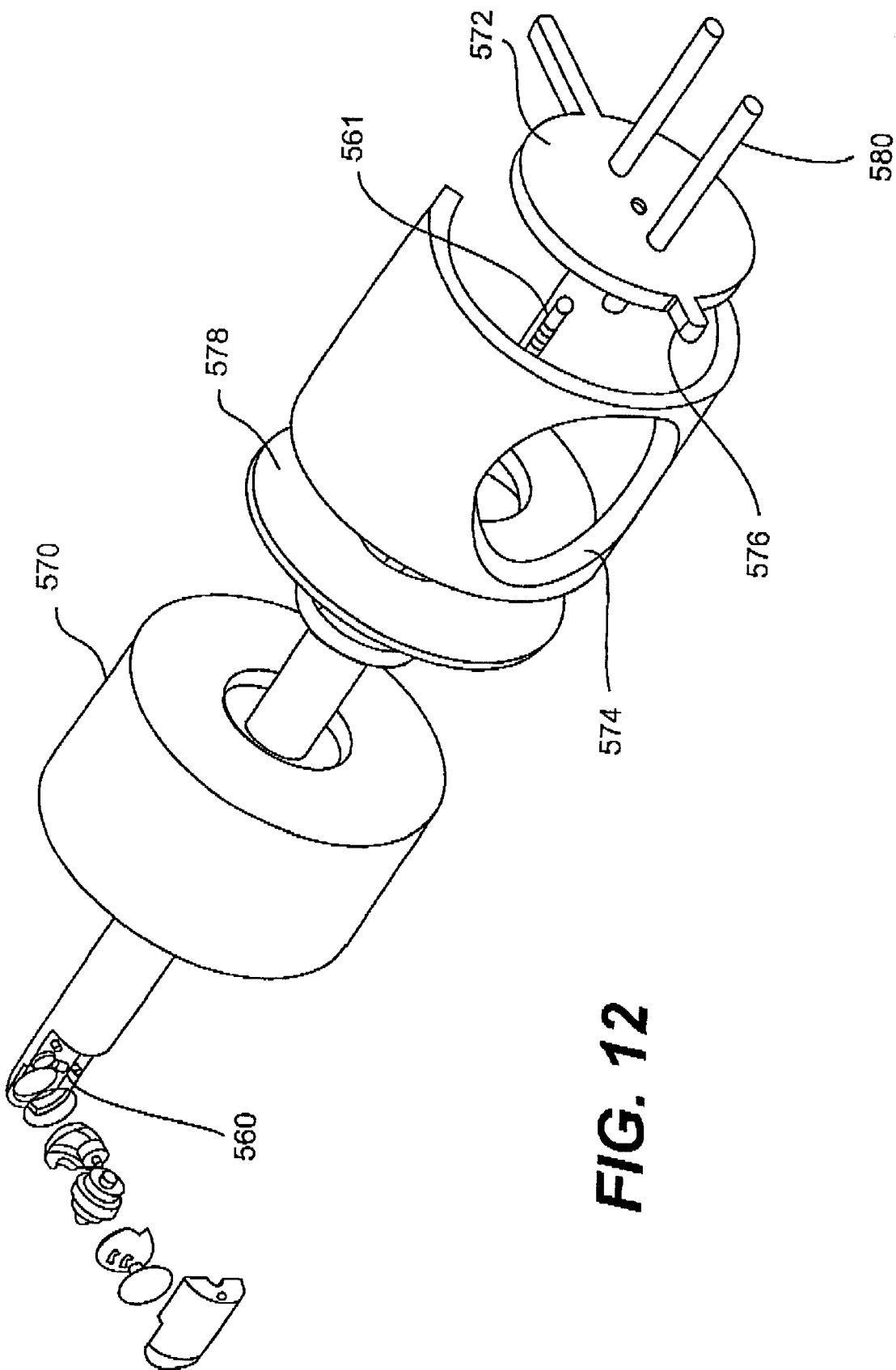
FIG. 12 is an exploded view of the miniaturized femur head cutter.
Figure 16:
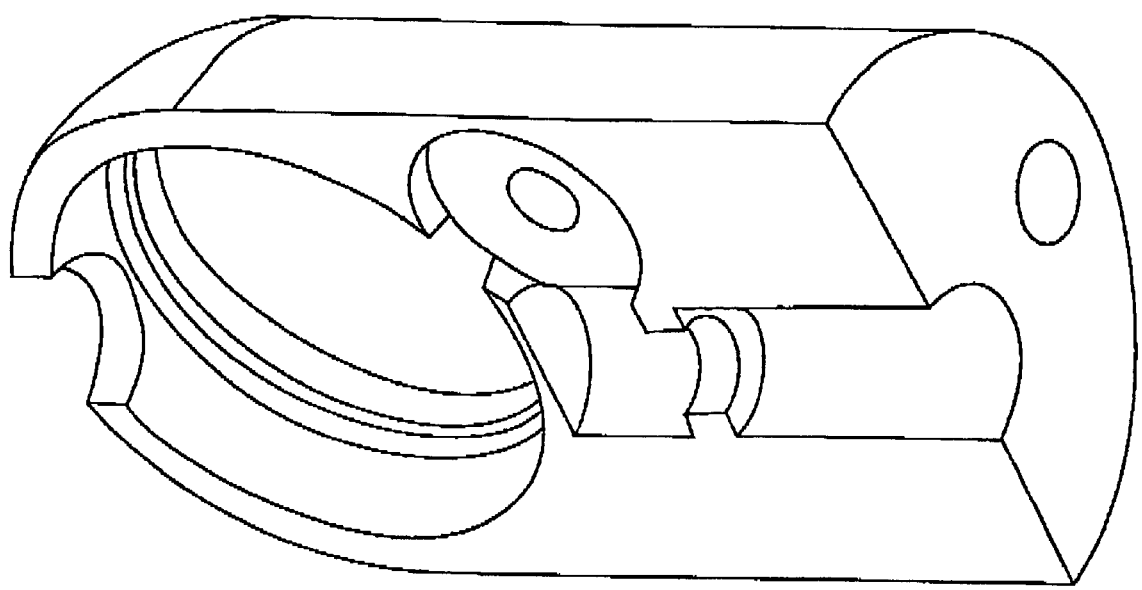
FIG. 16 is an isometric view of an outer cutter support housing of the present invention.
Figure 17B:
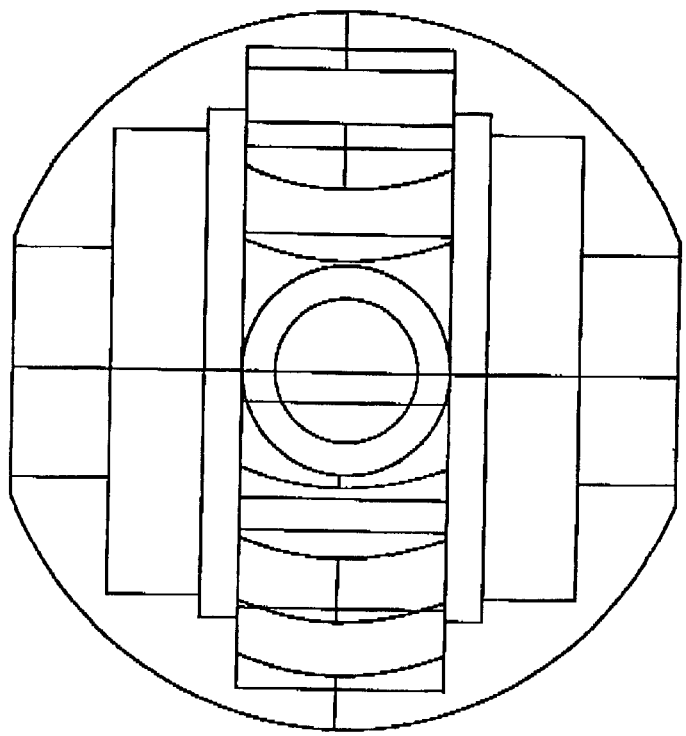
FIGS. 17A and 17B are isometric and top views, respectively, of a hemispherical turbine support housing according to the present invention.
Figure 17A:
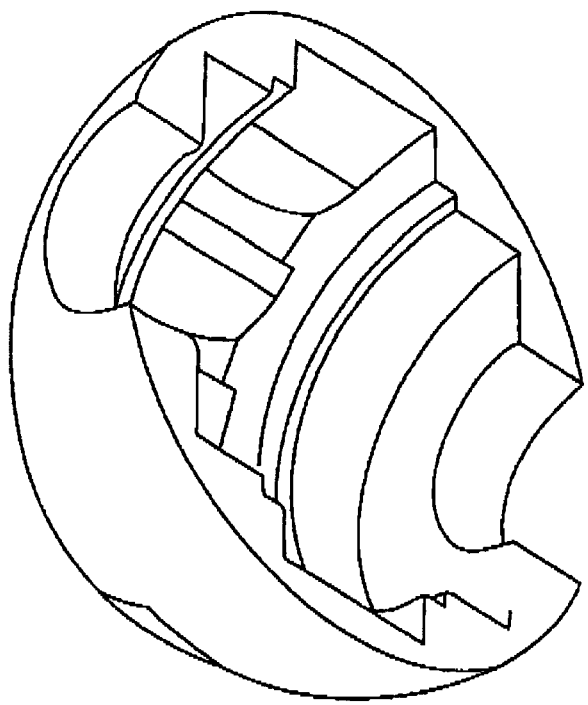
Figure 18:
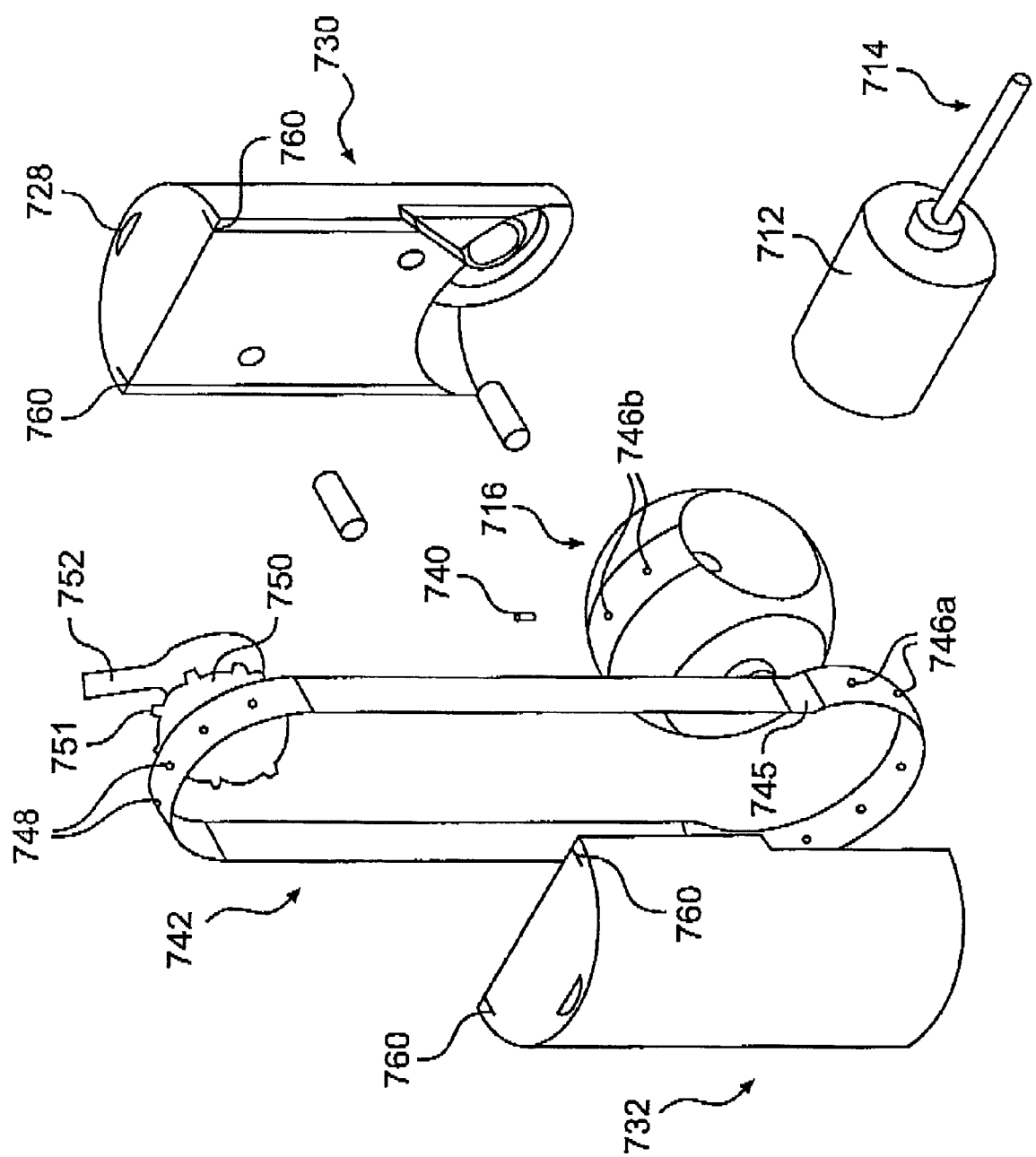
FIG. 18 is an exploded view of a second embodiment of the femur head cutter of the present invention.
Figure 19B:
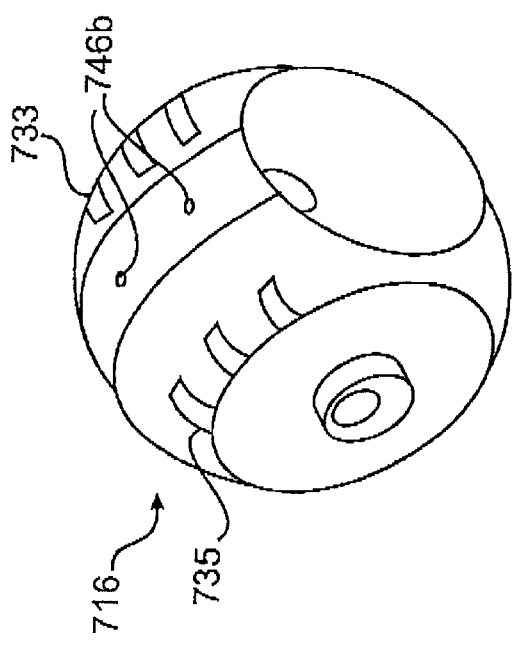
FIGS. 19A–19D are various views of the turbine support housing of the femur head cutter of FIG. 18.
Figure 19D:
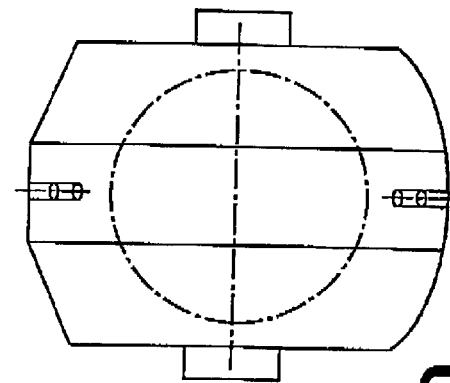
Figure 19C:
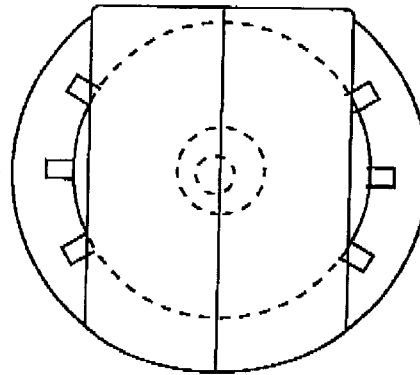
Figure 19A:
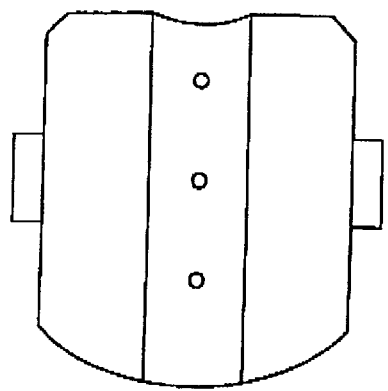
Figure 20D:
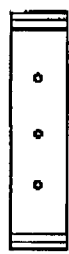
FIGS. 20A–20D are various views of the rotation belt of the femur head cutter of FIG. 18.
Figure 20C:
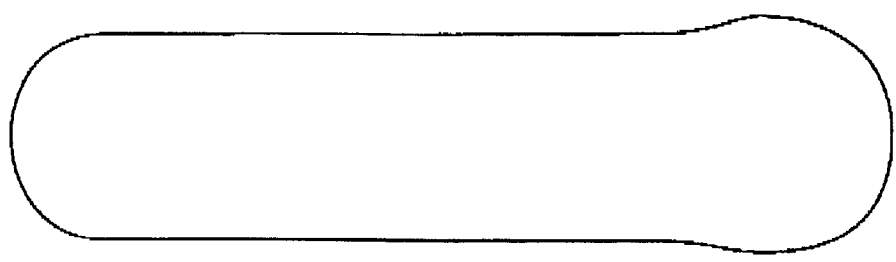
Figure 20B:
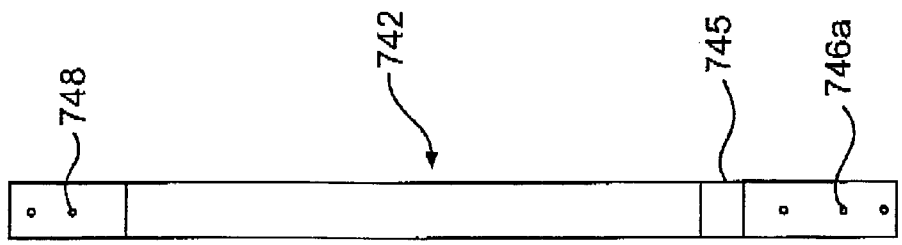
Figure 20A:
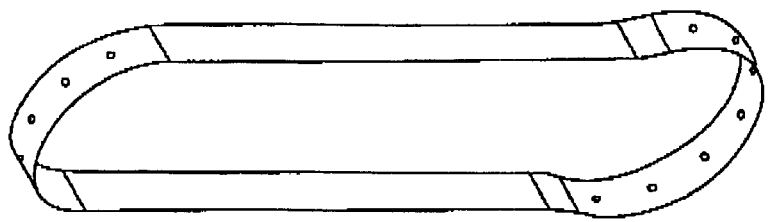

As shown in FIG. 12, the femur cutter 500 can be installed in a cutter guide assembly. The guide 570 is installed into a bore cut in the femur and locked in place. The guide 570 provides a rotational bearing surface for the longitudinal axis of the cutter support housing as well as a means for controlling the rotation angle about the longitudinal axis. The articulated cutting head is indexed by rotation of the threaded indexing shaft 560 which is engaged to the pinion gear 550 and ultimately engaged to the two hemispherical turbine support housing portions 532, 516. The indexing motion of the cutting head is coordinated with the longitudinal positioning of a cam follower plate 572. This is accomplished by threading the cam follower plate 572 and the corresponding section of the indexing shaft 560. Thus, when the indexing shaft 560 is turned to change the angle of the cutting head, the cam follower plate 572 moves along lithe indexing shaft threads 561. This causes the cam follower surface 574 on the plate 572 to contact a new section of the cam surface, thereby allowing the cutting tool 514 to traverse rotationally about the longitudinal axis of the cutting head support and to remove a greater or lesser amount of the bone surface.

Guide pins 580 bridge the distance from the cutter support housing flange surface to the maximum travel of the cam follower plate 572. Thus, when the cam follower plate handle is moved and a cam follower appendage 576 works within the restrictions of the cam surface, the cutting head also sweeps out the cam surface pattern as it cuts away the desired section of bone.

A retaining plate 578 is attached to the cutter guide housing to lock the cutter support housing into the guide housing, thus allowing only rotation of the cutter support housing and its associated cutting head and cutting tool.

An alternative embodiment of the miniaturized femur head cutter 700 is shown in FIGS. 18–20D. Instead of creating rotation of the cutting head with respect to the longitudinal axis of the cutting device by using gears and cam followers, a simpler mechanical structure is used. As embodied herein, the cutting assembly includes a turbine 712 having a cutting tool 714. Turbine 712 is supported in a spherical turbine housing 716, which is in turn supported within two halves of another cutter support housing 730, 732. Turbine housing 716 includes slots 733 to direct air received from air inlet 728 onto the blades of turbine 712 as discussed above. Turbine housing 716 is also connected via pins 740 to a belt 742. Belt 742 also includes a first set of connecting holes 746a. Connecting holes 746a align with connecting holes 746b in turbine housing 716 and belt 742 is held to turbine housing 716 by pins 740. Belt 742 also includes a second set of connecting holes 748, to engage a gear 750 connected to an actuation lever 752. As actuation lever 752 is moved, teeth 751 of gear 750, engaged in the second set of connecting holes 748 of belt 742, cause belt 742 to rotate within slots 760 of outer cutter support housings 730, 732. Belt 742 includes an open portion 745 to fit over cutting tool 714 and for engaging turbine 712. As belt 742 rotates, it causes turbine housing 716, and therefore turbine 712 and cutting tool 714 to rotate with it.

The present invention also includes a preferred method of operating a miniaturized femur cutter to remove an interior portion of a femur head. According to this method, a small incision is made into the skin below the hip of the patient, exposing the femur. A hole is drilled into the femur, and the device of the present invention is insert through the hole. Pressurized air is introduced into air inlet port 528 of outer cutter support housing 518. The air enters chamber 530, and then flows through slots 535 of hemispherical turbine support housing 516 to blades 524 of the turbine 512, causing the turbine 512 to spin at high speed. Ultimately this air exhausts out into the hemispherical support housing chamber 538 and out of air outlet passage 546 of outer cutter support housing 534 into the atmosphere.

The high speed rotation of the burr of turbine 512, allows cutting of the inside of the bone. In this instance, rotting, decayed, or cancerous sections of the femur head fare cut and removed. During the cutting process, the turbine support can be pivoted on axles 520 to change the cutting angle. Such pivoting is accomplished by rotating the indexing shaft 560 with respect to a longitudinal handle of the cutting device. As indexing shaft 560 rotates, it engages and causes pinion gear 550 to rotate, which in turn causes gear segment 548 to rotate, ultimately resulting in pivoting of turbine support 516, 532 about axles 520. Using controlled movement of the device, the cutting tool is used to sweep or cut out a section of the sphere forming the femur head.

It will be apparent to those skilled in the art that various modifications and variations can be made in the disclosed process and product without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A miniature cutting device comprising:

a turbine and burr;

a spherical turbine support housing, including two hemispherical turbine support housing portions, wherein the turbine support housing portions fit together to form the spherical turbine support housing and to hold the turbine and burr, and wherein a first hemispherical turbine support housing portion includes slots for directing air onto blades of the turbine to rotate the turbine;

two outer cutter assembly support housing portions, wherein each hemispherical turbine support housing portion is fitted to a respective outer cutter assembly support housing portion, wherein the outer cutter assembly support housing portion fitted to the first hemispherical turbine support housing includes an air inlet passage for supplying pressurized air to the slots of the first hemispherical turbine support housing; and means for rotating the turbine and burr about a longitudinal axis of the device.

2. The cutting device of claim 1, wherein the cutting device is a femur head cutting device.

3. The cutting device of claim 1, wherein the cutting device is a dental drill.

4. The cutting device of claim 1, wherein a second of the two hemispherical turbine support housings includes air directing slots for receiving air from the turbine blades and to direct the air toward an air outlet passage.

5. The cutting device of claim 4, wherein the outer cutter assembly support housing portion fitted to the second hemispherical turbine support housing includes the air outlet passage.

6. The cutting device of claim 1, wherein the means for rotating the turbine and burr about the longitudinal axis of the device includes a gear formed on the turbine support housing.

7. The cutting device of claim 1, wherein the means for rotating the turbine and burr about the longitudinal axis of the device includes a belt attached to the turbine support housing.

8. The cutting device of claim 7, wherein the means for rotating the turbine and burr about the longitudinal axis of the device further includes a gear and actuation lever, wherein a first end of the belt is connected to the spherical turbine housing and wherein a second end of the belt is connected to the gear.

9. A method of removing an interior portion of a femur head, comprising:

creating a small incision into skin below a hip of a patient to expose the femur;

drilling a small hole into the femur;

inserting a miniaturized femur cutter into the hole in the femur;

rotating a turbine and burr of the miniaturized femur cutter at a high speed to cut away a rotting, decayed, or cancerous section of the femur head;

changing the cutting angle as necessary by rotating the turbine and burr about a longitudinal axis of the miniaturized femur cutter; and removing the miniaturized femur cutter from the femur.

* * * * *